US006455732B1

(12) United States Patent
Aichinger et al.

(10) Patent No.: US 6,455,732 B1
(45) Date of Patent: Sep. 24, 2002

(54) METHOD FOR STORING AND/OR TRANSPORTING PURE ACRYLIC ACID

(75) Inventors: Heinrich Aichinger, Mannheim; Klaus Joachim Müller-Engel, Stutensee; Gerhard Nestler; Jürgen Schröder, both of Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/556,527

(22) Filed: Apr. 21, 2000

(30) Foreign Application Priority Data

May 21, 1999 (DE) .......................................... 199 23 389

(51) Int. Cl.$^7$ .......................... C07C 57/02; C07C 57/18; C07C 51/42
(52) U.S. Cl. .................. 562/598; 562/598; 562/600
(58) Field of Search .................... 562/598, 600

(56) References Cited

U.S. PATENT DOCUMENTS

| | | |
|---|---|---|
| 3,932,500 A | 1/1976 | Duembgen et al. |
| 4,622,425 A | * 11/1986 | Gagne |
| 5,504,247 A | 4/1996 | Saxer et al. |
| 5,877,344 A | * 3/1999 | Gande et al. |

FOREIGN PATENT DOCUMENTS

| | | |
|---|---|---|
| DE | 2 136 396 | 2/1973 |
| EP | 0 616 998 | 9/1994 |

OTHER PUBLICATIONS

W. Bauer article on "Acrylic Acid and Derivatives" in Kirk–Othmer Encyclopedia of Chemical Technology, 1991.*
Document No RD–0386003 filing date Jun. 1996 RD name Anon.*
Technische Information, TI/ED 1330 d of BASF Aktiengesellschaft, pp. 3–6, "Acrylsaeure Rein", Jun. 1992.
Kirk–Othmer, Encyclopedia of Chemical Technology, Fourth edition, vol. 1, p. 289, "Physical Properties of Acrylic Acid Derivatives", 1991.
Ullmanns Encyclopaedie der Technischen Chemie, 4$^{th}$ Edition, vol. 7, p. 85, "Acrylsaeure", 1994.

* cited by examiner

*Primary Examiner*—Johann Richter
*Assistant Examiner*—Farhad Forohar
(74) *Attorney, Agent, or Firm*—Oblon, Spivak, McClelland, Maier & Neustadt, P.C.

(57) ABSTRACT

Pure acrylic acid is stored and/or transported by a process in which the pure acrylic acid is stored and/or transported as liquid aqueous solution at ≦15° C.

27 Claims, No Drawings

METHOD FOR STORING AND/OR TRANSPORTING PURE ACRYLIC ACID

The present invention relates to a process for storing and/or transporting pure acrylic acid.

Acrylic acid, either as such or in the form of its salts or its esters, is important in particular for the preparation of polymers for a very wide range of applications (for example adhesives, superabsorbers or binders).

Acrylic acid is obtainable, inter alia, by catalytic gas-phase oxidation of propane, propene and/or acrolein. Said starting gases, as a rule diluted with inert gases such as nitrogen, $CO_2$ and/or steam, are passed as a mixture with oxygen at elevated temperatures and, if required, superatmospheric pressure over transition metal mixed oxide catalysts and are converted by oxidation into an acrylic acid-containing product gas mixture.

A basic separation of the acrylic acid from the product gas stream can be achieved by fractional condensation of the product gas mixture or by absorption in a suitable absorbent (for example water or a mixture of from 70 to 75% by weight of diphenyl ether and 25 to 30% by weight of diphenyl) (cf. for example EP-A 297 445 and German Patent 2,136,396).

An acrylic acid which is referred to here as crude acrylic acid is usually obtained by removal of the absorbent (if necessary after prior desorption of impurities having low absorbent solubility by stripping, for example using air) by extractive and/or distillative separation processes (for example, removal of the absorbent water by distillation, azeotropic distillation and/or extractive separation of the acid from the aqueous solution and subsequent removal of the extracting agent by distillation) and/or after the use of other separation steps (for example crystallization).

This crude acrylic acid is not a pure product. Rather, it contains a range of different impurities typical of the preparation route by gas-phase catalytic oxidation. These are in particular acetic acid, propionic acid, water and low molecular weight aldehydes, such as acrolein, methacrolein, propionaldehyde, n-butyraldehyde, benzaldehyde, furfurals and crotonaldehyde.

Further undesired impurities of acrylic acid present in the condensed phase are the acrylic acid oligomers (Michael adducts) formed by Michael addition of acrylic acid with itself and with the resulting acrylic acid dimers. For statistical reasons essentially only the formation of diacrylic acid

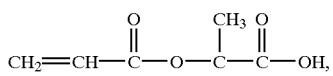

is of importance, whereas the formation of higher acrylic acid oligomers (trimers, tetramers, etc.) can be for the most part neglected (in this publication, acrylic acid oligomer is always understood as meaning the corresponding Michael adducts and acrylic acid oligomers not formed by radical polymerization, so that the formation of the latter is essentially suppressed by the presence of polymerization inhibitors).

If such a crude acrylic acid were used directly as an acrylic acid source in free radical polymerization, the compounds not capable of free radical polymerization, acetic acid and propionic acid, would remain, for example, as volatile compounds, in the polymerization product which is undesirable for numerous uses of the polymerization products, owing to the resulting annoying odor. Furthermore, the content of low molecular weight aldehydes in such a crude acrylic acid adversely affects free radical polymerizations as a rule in that the aldehyde impurities, for example, influence the induction time of free radical polymerizations, i.e. the period between reaching the polymerization temperature and the actual beginning of the polymerization. Moreover, they generally influence the degree of polymerization and can also give rise discolorations in the polymers.

In addition, acrylic acid must contain as far as possible no diacrylic acid since diacrylic acid has a less pronounced tendency to free radical polymerization than acrylic acid. Moreover, in the case of diacrylic acid copolymerized with the aid of free radicals, there is the danger that monomeric acrylic acid will be eliminated on subsequent thermal treatment, which as a rule is undesirable. The abovementioned applies in particular when the acrylic acid is used for the preparation of superabsorbers (=materials for absorbing water and based on polyacrylic acid and its salts), since diacrylic acid not polymerized with the aid of free radicals and acrylic acid are particularly undesirable in superabsorber applications (superabsorbers are used in particular in the hygiene sector (for example in babies' diapers); a content of uncopolymerized diacrylic acid and acrylic acid is essentially not tolerable in this sector).

It is therefore the object of the acrylic acid producers substantially to separate off said impurities from crude acrylic acid. This can be done by purification by, for example, rectification and/or, as described in EP-A 616 998, by crystallization.

Acrylic acid whose purity is $\geq 98\%$ by weight, based on the sum of all components present (including the polymerization inhibitor usually added for preventing undesired premature free radical polymerization of the acrylic acid), is obtainable, i.e. it contains at least 98%, based on its weight, of acrylic acid molecules. In this publication acrylic acids of this purity are to be summarized under the general term "pure acrylic acid".

In this publication, pure acrylic acids are therefore in particular those acrylic acids whose purity, based in the same way as above on the sum of all components present, is $\geq 98.5$ or $\geq 99$ or $\geq 99.5$ or $\geq 99.75$ or $\geq 99.9\%$ by weight.

Usually, preparation of pure acrylic acid is carried out by direct further processing of freshly prepared crude acrylic acid since the latter still contains virtually no resultant acrylic acid oligomers. Produced pure acrylic acid is usually freshly consumed.

However, it may be necessary from case to case to store pure acrylic acid over a relatively long period and/or to transport it over relatively long distances. The fact that undesired diacrylic acid is formed in an increasing amount within the pure acrylic acid in an essentially uncontrollable manner during the storage and/or transportation time proves disadvantageous.

The Technical Information TI/ED 1330 d (June 1992) of BASF Aktiengesellschaft discloses that the diacrylic acid formation in pure acrylic acid is promoted by higher storage temperature and by the presence of water (which is why pure acrylic acid is usually essentially freed from water). In addition, said Technical Information notes that the formation of diacrylic acid taking place within the pure acrylic acid cannot be prevented by any chemical additives and that the diacrylic acid formation in pure acrylic acid containing less than 0.1% by weight of water is from about 0.5 to 1% by weight, based on the content of acrylic acid, per month.

The measure essentially remaining according to the above for reducing diacrylic acid formation in pure acrylic acid which has been stored and/or transported is thus to store and/or to transport the pure acrylic acid on the one hand as far as possible in the absence of water and on the other hand at as low a temperature as possible.

Of importance in this context is the fact that the solidification point of acrylic acid is at comparatively high temperatures (according to the abovementioned TI/ED 1330 d (June 1992) of BASF Aktiengesellschaft, the freezing point of acrylic acid (at a pressure of 1 bar) is 13° C.; according to Kirk-Othmer, Encyclopedia of Chemical Technology, Fourth Edition, Vol. 1, John Wiley & Sons, New York (1991), page 289, the corresponding freezing point of acrylic acid is 13.5° C.).

Thus, in order to suppress diacrylic acid formation in pure acrylic acid very effectively, it is necessary, according to the prior art, to store and/or to transport the pure acrylic acid in the absence of water at temperatures as low as possible in the solid state.

According to Ullmanns Encyclopadie der technischen Chemie, 4th Edition, vol. 7 (1994), Verlag Chemie, page 85, column 2, however, the thawing of frozen pure acrylic acid requires extreme caution because the pure acrylic acid becomes locally depleted in polymerization inhibitor on freezing (the applicability of fractional crystallization as a purification method is based precisely on this phase separation) and destabilized acrylic acid can polymerize explosively with considerable heat evolution. The abovementioned applies particularly when polymerization is inhibited by means of inhibitors which display. their full power only in the presence of molecular oxygen (e.g. hydroquinone monomethyl ether and/or hydroquinone monoethyl ether), because the crystallization process is also associated with considerable local depletion of the stabilizing dissolved oxygen in the acrylic acid. In these cases, for safety reasons, the frozen pure acrylic acid must be thoroughly mixed from time to time with admission of air during melting, in order to bring about uniform oxygen saturation as soon as possible. Moreover, for safety reasons, the external heat source used for thawing may not have too high a temperature level, and the thawing therefore takes a comparatively long time, in which once again undesired diacrylic acid formation takes place.

In practice, pure acrylic acid is therefore stored and/or transported at temperatures of $\geq 15°$ C., i.e. a safety margin of at least 2° C. relative to the freezing point of acrylic acid is usually maintained since fluctuations in the functionality of the thermostat unit used cannot be completely ruled out.

However, according to our investigations into pure acrylic acid having a purity of $\geq 99.8\%$ by weight and a water content of $\leq 0.05\%$ by weight, the disadvantage of the abovementioned procedure is that, on the one hand, the rate of the diacrylic acid formation at 15° C. is as much as 40 ppm by weight per day (24 h) (at a pressure of 1 atm; this boundary condition is always to apply in this publication unless expressly stated to the contrary) and, on the other hand, the safety margin of 2° C. maintained is comparatively small.

It is an object of the present invention to provide an improved process for storing and/or transporting pure acrylic acid, which process at least partially remedies the disadvantages of the prior art processes.

We have found that this object is achieved by a process for storing and/or transporting pure acrylic acid, wherein the pure acrylic acid is stored and/or transported as a liquid aqueous solution with the proviso that a) the water content of the aqueous pure acrylic acid solution is at least 5% by weight, based on the weight of the aqueous pure acrylic acid solution, b) the content of chemical compounds, other than water and acrylic acid, in the aqueous pure acrylic acid solution is not more than 2% by weight, based on the weight of the acrylic acid present in the aqueous pure acrylic acid, and c) the temperature of the aqueous pure acrylic acid solution during storage and/or transportation is $\leq 15°$ C.

The novel process is based on the surprising experimental finding that, on adding water to pure acrylic acid, on the one hand the rate of the diacrylic acid formation (in this publication it is always based on the amount of acrylic acid present) increases but, on the other hand, the increase in the rate of the diacrylic acid formation reverses, i.e. becomes smaller, with increasing amount of water and a pronounced freezing point depression is associated with the addition of water.

The abovementioned effects make it possible, in an unexpected manner, to cool aqueous solutions of pure acrylic acid, while maintaining the liquid state, at a temperature which is such that, with a predetermined difference (safety margin) relative to the freezing point, a lower level of diacrylic acid formation takes place in the aqueous pure acrylic acid solution than in the associated pure acrylic acid.

Thus, the diacrylic acid formation in a pure acrylic acid having a purity of $\geq 99.8\%$ by weight and a water content of $\leq 0.05\%$ by weight at 25° C. (difference from freezing point=12° C.) is 285 ppm by weight/day. If water is added to such a pure acrylic acid, the freezing point of the resulting aqueous pure acrylic acid solutions decreases as a function of the water content to the following values:

| Water content (% by weight, based on solution) | Freezing point (° C.) |
| --- | --- |
| 10 | +2 |
| 20 | −5 |
| 30 | −10 |
| 40 | −12 |
| 50 | −9 |

At +15° C. (difference from the freezing point in all cases $\geq 13°$ C.), the diacrylic acid formation in all abovementioned aqueous solutions is however <190 ppm by weight/day (based on the weight of the acrylic acid present in the aqueous solution).

The novel process is suitable for pure acrylic acids having a purity (acrylic acid oligomers are considered as impurities) of $\geq 98$ or $\geq 98.5$ or $\geq 99$ or $\geq 99.5$ or $\geq 99.75$ or $\geq 99.9\%$ by weight.

The novel storage and/or transportation can be effected in all abovementioned cases in the form of aqueous pure acrylic acid solution whose water content, based on the weight of the aqueous solution, is from 5 to 80 or from 5 to 70 or from 5 to 60 or from 5 to 50 or from 5 to 40 or from 5 to 30 or from 5 to 20 or from 5 to 10% by weight. However, the lower limit in all abovementioned quantity ranges may also be 10 or 15 or 20 or 25 or 30 or 35 or 40 or 45 or 50 or 55 or 60% by weight. In a corresponding manner, the upper limit of said quantity ranges may also be 75 or 65 or 55 or 45 or 35 or 25 or 15% by weight.

In all abovementioned cases, the temperature of the aqueous pure acrylic acid solution during the novel storage and/or transportation may be $\leq 14°$ C., $\leq 12°$ C., $\leq 10°$ C., $\leq 8°$ C., $\leq 7°$ C., $\leq 5°$ C., $\leq 3°$ C., $\leq 1°$ C., $\leq 0°$ C., $\leq -2°$ C., $\leq -4°$ C., $\leq -5°$ C., $\leq -7°$ C., $\leq -9°$ C., $\leq -10°$ C. or $\leq -11°$ C., as long as the temperature during storage and/or transportation is only above the respective freezing point.

Frequently, the temperature during storage and/or transportation in the novel process will therefore be $\geq-15°$ C. or $\geq-12°$ C. or $\geq-10°$ C. or $\geq-8°$ C. or $\geq-5°$ C. or $\geq-2°$ C. or $\geq 0°$ C. or $\geq+2°$ C. or $\geq 5°$ C. or $\geq 7°$ C. or $\geq 10°$ C.

The particular attraction of the novel process is based on the fact that the use of pure acrylic acid in polymerization is effected predominantly in an aqueous medium (for example, the preparation of superabsorber polymers was carried out by free radical polymerization of acrylic acid and/or its water-soluble salts in aqueous solution (see for example U.S. Pat. No. 4,931,497); however, the production of emulsion polymers containing acrylic acid and/or its salts ascopolymerized unit is also effected in an aqueous medium). Thus, after the end of storage and/or transportation, the novel aqueous pureacrylic acid solutions can as a rule be used directly as such for the intended use of the pure acrylic acid, since the presence of water in these applications presents no problems in the predominant number of cases.

The latter also applies when pure acrylic acid is used for the preparation of esters, since water is a typical byproduct of an esterification.

Of course, the novel storage and/or transportation of aqueous pure acrylic acid solutions is usually carried out in the presence of polymerization inhibitors, although pure acrylic acid diluted with water presumably has, based on the amount of acrylic acid present, a lower inhibitor requirement than the pure acrylic acid itself for stabilizing it against undesired premature free radical polymerization.

Suitable polymerization inhibitors to be used are in principle all known acrylic acid polymerization inhibitors. They are preferably soluble in the aqueous pure acrylic acid solution in the amount to be used. The amount to be used is usually $\leq 1000$ pm by weight, based on the amount of acrylic acid present.

Typically, the polymerization inhibitor content in the novel process is $\geq 10$ ppm by weight (on the same basis).

Typical polymerization inhibitor contents are from 50 to 750 or from 75 to 500 or from 100 to 400 or from 100 to 300 ppm by weight. Examples of suitable polymerization inhibitors to be used according to the invention are those of EP-A 765 856, of EP-A 685 447, of JP-A 7-53449, of JP-A 6-345681, of EP-A 620 206, of the Chemical Journal of Chinese Universities, Vol. 4, No. 2, 1983, of JP-A 6-192335, of JP-A 320217, of JP-A 5-320217, of EP-A 467851, of EP-A 178168, of CN-A 1052847, of WO 92/1665, of CN-A 86103840, of DE-A 1618141, of German Patent 1543996, of DE-A 2931553 and of EP-A 685447. The polymerization inhibitors stated in the abovementioned publications may be used in each case individually or in the combinations recommended in these publications. The polymerization inhibitors stated in Wo 9921893 are also suitable according to the invention, both when used individually and when used in the combinations recommended therein.

Examples of typical such polymerization inhibitors are molecular oxygen, phenothiazines, phenol compounds, N-oxyl radicals, nitroso compounds and p-phenylenediamines. Suitable individual members of these groups are phenothiazine, hydroquinone, the monomethyl ether of hydroquinone, the monoethyl ether of hydroquinone, 4-hydroxy-2,2,6,6-tetramethyl-1-oxylpiperidine, benzoquinone, 4-nitrosophenol and p-phenylenediamine.

Expediently, exclusively hydroquinone or only the monomethyl ether of hydroquinone or only the monoethyl ether of hydroquinone or mixtures of two or all three of said hydroquinone compounds are present as polymerization inhibitors in the novel process. Regarding the amount of them which is used, what was said at the outset is applicable, i.e. they are used as a rule in amounts of $\leq 5000$ ppm by weight or $\leq 2000$ ppm by weight, in general $\leq 1000$ ppm by weight, frequently $\leq 500$ ppm by weight, often $\leq 300$ ppm by weight, in some cases $\leq 200$ ppm by weight, but as a rule $\geq 10$ ppm by weight, usually $\geq 50$ ppm by weight, based on the amount of acrylic acid present in the aqueous pure acrylic acid solution.

The content of other polymerization inhibitors in the aqueous pure acrylic acids to be treated according to the invention is at the same time altogether $\leq 20$ or $\leq 10$ or $\leq 5$ and particularly expediently $\leq 2$ or $\leq 1$ ppm by weight, based in a corresponding manner on the acrylic acid content. The abovementioned values also apply in particular to an individual content of phenothiazine.

The novel process is particularly suitable when the storage and/or transportation time is at least 1 day or at least 2 days or at least 3 days or at least 4 days or at least 5 days or at least 6 days or at least 7 days. However, it may also be $\geq 10$ days or $\geq 20$ days or $\geq 30$ days or $\geq 40$ days or $\geq 50$ days. Expediently, the storage and/or transportation time in the novel process is $\leq 6$ months, frequently $\leq 5$ months, often $\leq 4$ months, in general $\leq 3$ months and in many cases $\leq 2$ months or $\leq 1$ month.

The diacrylic acid content of the aqueous pure acrylic acid solutions to be stored according to the invention is $\leq 20,000$ ppm by weight, based on the content of acrylic acid. In general, the diacrylic acid content, on the above basis, is $\leq 15,000$, often $\leq 10,000$, in many cases $\leq 8000$, frequently $\leq 6000$ or $\leq 4000$ ppm by weight.

However, the novel process can be applied in particular to those aqueous pure acrylic acid solutions whose diacrylic acid content, based on the acrylic acid content, is $\leq 3000$ or $\leq 2000$ or $\leq 1500$ or $\leq 1000$ ppm by weight, but also $\leq 750$ or $\leq 500$, in many cases $\leq 250$ or $\leq 100$ or $\leq 50$ or $\leq 25$ ppm by weight.

Likewise, the aldehyde content of the aqueous pure acrylic acid solutions to be stored and/or to be transported according to the invention is $\leq 20,000$ ppm by weight, based on the acrylic acid content. In general, the aldehyde content, on the above basis, is $\leq 15,000$, often $\leq 10,000$, in many cases $\leq 8000$, frequently $\leq 6000$ or $\leq 4000$ ppm by weight.

However, the novel process can be applied in particular to those aqueous pure acrylic acid solutions whose aldehyde content, based on the acrylic acid content, is $\leq 3000$ or $\leq 2000$ or $\leq 1500$ or $\leq 1000$ ppm by weight, but also $\leq 750$ or $\leq 500$, in many cases $\leq 250$ or $\leq 100$ or $\leq 50$ or $\leq 25$ ppm by weight. Of course, the aldehyde content, on the above basis, of the aqueous pure acrylic acid solution to be treated according to the invention may also be $\leq 20$ or $\leq 15$ ppm by weight, but also $\leq 10$ or $\leq 5 \leq 1$ or $\leq 0.5$ or 0.1 ppm by weight.

However, the novel process may also be applied to those aqueous pure acrylic acid solutions whose total content of acetic acid and propionic acid, based on the acrylic acid present, is $\leq 15,000$ or $\leq 10,000$, in many cases $\leq 8000$, frequently $\leq 6000$ or 4000 or $\leq 3000$ or $\leq 2000$ or $\leq 1000$ or $\leq 500$ ppm by weight.

The novel process can therefore be applied in particular to pure crylic acid for which the following are applicable (based on their total weight):

a) acrylic acid content $\geq 99\%$ by weight, diacrylic acid content $\leq 6000$ ppm by weight, aldehyde content $\leq 10$ ppm by weight, content of monomethyl ether of hydroquinone (MEHQ) and of monoethyl ether of hydroquinone (EEHQ) together $\leq 1000$ ppm by weight and $\geq 20$ ppm by weight, phenothiazine content $\leq 5$ ppm by weight and content of acetic acid and propionic acid together ≦6000 ppm by weight;

or b) acrylic acid content ≧99.5% by weight, diacrylic acid content ≦4000 ppm by weight, aldehyde content ≦5 ppm by weight, content of MEHQ and EEHQ together ≦500 ppm by weight and ≧20 ppm by weight, phenothiazine content ≦3 ppm by weight and content of acetic acid and propionic acid together ≦4000 ppm by weight;

or c) acrylic acid content ≧99.8% by weight, diacrylic acid content ≦2000 ppm by weight, aldehyde content ≦1 ppm by weight, content of MEHQ and EEHQ together ≦250 ppm by weight and ≧20 ppm by weight, phenothiazine content ≦1 ppm by weight and content of acetic acid and propionic acid together ≦2000 ppm by weight;

or d) acrylic acid content ≧99.8% by weight, diacrylic acid content ≦500 ppm by weight, aldehyde content: ≦1 ppm by weight per aldehyde, MEHQ content from 100 to 300 ppm by weight, phenothiazine content ≦1 ppm by weight and content of acetic acid and propionic acid together ≦1500 ppm by weight.

EXAMPLES

Freshly prepared pure acrylic acid having the following specification:

≧99.8% by weight of acrylic acid,

≦0.005% by weight of water, 200 ppm by weight of MEHQ,

≦1 ppm by weight of phenothiazine,

≦3 ppm by weight of aldehyde,

≦1500 ppm by weight of acetic acid and propionic acid and

≦500 ppm by weight of diacrylic acid were stored as such in the form of various aqueous solutions at various temperatures and in each case the rate of diacrylic acid formation (ppm by weight/day) was determined. The results of the diacrylic acid formation (based in each case on the amount of acrylic acid present) which are obtained as a function of the water content (% by weight, based on the total weight) and of the temperature are shown in the table below. Furthermore, the table contains the associated freezing point mp in 0° C. in each case.

| T (° C.) | H₂O (% by weight) | | | | | |
|---|---|---|---|---|---|---|
| | <0.005 | 10 | 20 | 30 | 40 | 50 |
| −5 | — | — | — | <10 | <10 | — |
| 0 | — | — | — | 48 | 43 | — |
| 5 | — | 75 | 92 | 87 | 75 | 63 |
| 15 | 40 | 189 | 219 | 204 | 157 | 150 |
| 25 | 287 | 1023 | 1207 | 1057 | 940 | 718 |
| | mp = +13 | mp = +2 | mp = −5 | mp = −10 | mp = −12 | mp = −9 |

We claim:

1. A process for storing and/or transporting pure acrylic acid, wherein the pure acrylic acid is stored and/or transported as a liquid aqueous solution with the proviso that
   a) the water content of the aqueous pure acrylic acid solution is at least 5% by weight, based on the weight of the aqueous pure acrylic acid solution,
   b) the content of chemical compounds, other than water and acrylic acid, in the aqueous pure acrylic acid solution is not more than 2% by weight, based on the weight of the acrylic acid present in the aqueous pure acrylic acid, and
   c) the temperature of the aqueous pure acrylic acid solution during storage and/or transportation is ≦15° C.

2. A process as claimed in claim 1, wherein the content of chemical compounds, other than water and acrylic acid, in the aqueous pure acrylic acid solution is ≦1% by weight, based on the weight of the acrylic acid present in the aqueous pure acrylic acid solution.

3. A process as claimed in claim 1, wherein the content of chemical compounds, other than water and acrylic acid, in the aqueous pure acrylic acid solution is ≦0.5% by weight, based on the weight of the acrylic acid present in the aqueous pure acrylic acid solution.

4. A process as claimed in claim 1, wherein the content of chemical compounds, other than water and acrylic acid, in the aqueous pure acrylic acid solution is ≦0.2% by weight, based on the weight of the acrylic acid present in the aqueous pure acrylic acid solution.

5. A process as claimed in claim 1, wherein the water content of the aqueous pure acrylic acid solution is from 5 to 50% by weight, based on the weight of the aqueous pure acrylic acid solution.

6. A process as claimed in claim 1, wherein the water content of the aqueous pure acrylic acid solution is from 10 to 40% by weight, based on the weight of the aqueous pure acrylic acid solution.

7. A process as claimed in claim 1, wherein the water content of the aqueous pure acrylic acid solution is from 10 to 30% by weight, based on the aqueous pure acrylic acid solution.

8. A process as claimed in claim 1, wherein the temperature of the aqueous pure acrylic acid solution during storage and/or transportation is ≦10° C.

9. A process as claimed in claim 1, wherein the temperature of the aqueous pure acrylic acid solution during storage and/or other transportation is ≦5° C.

10. A process as claimed in claim 1, wherein the aqueous pure acrylic acid solution contains, as polymerization inhibitor, the monomethyl ether of hydroquinone and/or monoethyl ether of hydroquinone, and the content of other polymerization inhibitors in the aqueous pure acrylic acid solution is ≦20 ppm by weight, based on the weight of the acrylic acid present.

11. A process as claimed in claim 10, wherein the phenothiazine content of the aqueous pure acrylic acid solution is ≦2 ppm by weight, based on the weight of the acrylic acid present therein.

12. A process as claimed in claim 1, wherein the aldehyde content of the aqueous pure acrylic acid solution is ≦10 ppm by weight, based on the weight of the acrylic acid present therein.

13. A process as claimed in claim 1, wherein the diacrylic acid content of the aqueous pure acrylic acid solution is ≦2000 ppm by weight, based on the weight of the acrylic acid present therein.

14. A process as claimed in claim 1, wherein the content of the acetic acid and propionic acid together in the aqueous pure acrylic acid solution is ≦2000 ppm by weight, based on the weight of the acrylic acid present therein.

15. A process as claimed in claim 1, wherein the storage and/or transportation time is at least 1 day.

16. A process as claimed in claim 1, wherein the storage and/or transportation time is at least 2 days.

17. A liquid aqueous pure acrylic acid solution whose water content, based on the weight of said solution, is at least 5% by weight and whose content of chemical compounds, other than water and acrylic acid, is not more than 2% by weight, based on the weight of the acrylic acid present in the aqueous pure acrylic acid solution, and whose temperature is $\leq 15°$ C.

18. A liquid aqueous pure acrylic acid solution as claimed in claim 17, whose content of chemical compounds, other than water and acrylic acid, is $\leq 1\%$ by weight, based on the weight of the acrylic acid present in the aqueous pure acrylic acid solution.

19. A liquid aqueous pure acrylic acid solution as claimed in claim 17, whose content of chemical compounds, other than water and acrylic acid, is $\leq 0.5\%$ by weight, based on the weight of the acrylic acid present in the aqueous pure acrylic acid solution.

20. A liquid aqueous pure acrylic acid solution as claimed in claim 17, whose content of chemical compounds, other than water and acrylic acid, is $\leq 0.3\%$ by weight, based on the weight of the acrylic acid present in the aqueous pure acrylic acid solution.

21. A liquid aqueous pure acrylic acid solution as claimed in claim 17, whose diacrylic acid content is $\leq 2000$ ppm by weight, based on the weight of the acrylic acid present in the aqueous pure acrylic acid solution.

22. A liquid aqueous pure acrylic acid solution as claimed in claim 17, whose temperature is $\leq 10°$ C.

23. A liquid aqueous pure acrylic acid solution as claimed in claim 17, whose temperature is $\leq 5°$ C.

24. A liquid aqueous pure acrylic acid solution as claimed in claim 17, whose temperature is $\leq 0°$ C.

25. A liquid aqueous pure acrylic acid solution as claimed in claim 17, whose water content is at least 10% by weight, based on the weight of said solution.

26. A liquid aqueous pure acrylic acid solution as claimed in claim 17, whose content of monoethyl ether of hydroquinone is $\geq 20$ ppm by weight and $\leq 500$ ppm by weight, based on the weight of the acrylic acid present in the aqueous pure acrylic acid solution.

27. A liquid aqueous pure acrylic acid solution as claimed in claim 17, whose aldehyde content is $\leq 10$ ppm by weight, based on the weight of the acrylic acid present in the aqueous pure acrylic acid solution.

* * * * *